United States Patent [19]

Kolassa et al.

[11] Patent Number: 5,994,369
[45] Date of Patent: Nov. 30, 1999

[54] SUBSTITUTED PIPERIDINE OR PYRROLIDINE COMPOUNDS FOR TREATING SIGMA-RECEPTOR MODULATED DISORDERS

[75] Inventors: Norbert Kolassa, Constance; Johannes Kornhuber, Würzburg, both of Germany

[73] Assignee: Byk Gulden Lomberg Chemische Fabrik GmbH, Constance, Germany

[21] Appl. No.: 08/930,642

[22] PCT Filed: Apr. 2, 1996

[86] PCT No.: PCT/EP96/01442

§ 371 Date: Oct. 6, 1997

§ 102(e) Date: Oct. 6, 1997

[87] PCT Pub. No.: WO96/31208

PCT Pub. Date: Oct. 10, 1996

[30] Foreign Application Priority Data

Apr. 5, 1995 [CH] Switzerland ............... 976/95

[51] Int. Cl.[6] .................................. A61K 31/445
[52] U.S. Cl. ............................................ 514/317
[58] Field of Search ............................. 514/317

[56] References Cited

FOREIGN PATENT DOCUMENTS 1967186 11/1980 Germany .
9500131 1/1995 WIPO .

OTHER PUBLICATIONS

Hudkins et al., Life Sci., 49(1), 1229–35, 1991.
Walker et al., Pharmacological Reviews, 42(4), 355–402, 1990.

*Primary Examiner*—Phyllis G. Spivack
*Attorney, Agent, or Firm*—Jacobson, Price, Holman & Stern, PLLC

[57] ABSTRACT

The invention concerns the use of compounds of formula (I), in which $R^1$, $R^2$, $R^3$, $R^4$, $R^5$, m and n have the meanings indicated herein for use in the treatment of sigma-receptor modulated disorders.

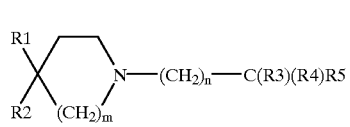

(I)

8 Claims, No Drawings

SUBSTITUTED PIPERIDINE OR PYRROLIDINE COMPOUNDS FOR TREATING SIGMA-RECEPTOR MODULATED DISORDERS

FIELD OF APPLICATION OF THE INVENTION

The invention relates to the novel use of known active compounds in the treatment of illnesses which are favorably affected by substances having affinity for sigma receptors.

KNOWN TECHNICAL BACKGROUND

British Patent 1313781 describes substituted piperidines which are distinguished by a long-lasting, centrally stimulating action. One of the active compounds coming under the British patent, for which the INN budipine was later recommended, is being tested in the therapy of Parkinsonism. Furthermore, the prior art (e.g. German Patent Specification 10 05 067, German Patent Specification 871 899, German Patent Specification 875 660, East German Patent Specification 50 603 and U.S. Pat. No. 2,411,664) discloses a number of 1-pyrrolidino- and 1-piperidinopropanols and -butanols, such as, for example, biperidin, cycrimine, pridinol, procyclidine, trihexyphenidyl, triperidin or difenidol, which in some cases can likewise be employed in the therapy of Parkinsonism.

DESCRIPTION OF THE INVENTION

Surprisingly, it has now been found that the compounds described below in greater detail have a high affinity for sigma receptors and are therefore advantageously suitable for the treatment of illnesses which can be favorably affected by alterations in the function of sigma receptors.

The invention relates to the use of compounds of the formula I

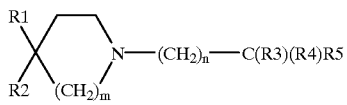

(I)

in which either
R1 is phenyl,
R2 is phenyl,
R3 is hydrogen or 1-4C-alkyl,
R4 is hydrogen or 1-4C-alkyl,
R5 is hydrogen or 1-4C-alkyl,
m is the number 2
and
n is the number 0,
or in which
R1 is hydrogen,
R2 is hydrogen,
R3 is phenyl,
R4 is cyclopentyl, cyclohexyl, phenyl, 2-norbornen-5-yl or tricyclo[2.2.1.0$^{2,6}$]hept-2-yl,
R5 is hydroxyl
m is the number 1 or 2
and
n is the number 2 or 3,
and their salts for the production of medicaments for the treatment of sigma receptor-modulated illnesses.

1-4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and, in particular, the methyl radical.

Suitable salts of compounds of the formula I are preferably all pharmacologically tolerable acid addition salts with the inorganic and organic acids customarily used in pharmacy. Those which are suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, it being possible to employ the acids in salt preparation - depending on whether it is a mono- or polybasic acid and depending on which salt is desired—in an equimolar quantitative ratio or one differing therefrom.

Depending on the nature of the substituents, the compounds of the formula I can be optically active compounds. The invention therefore includes both the enantiomers and their mixtures and racemates.

Illnesses which may be mentioned which are favorably affected by substances having affinity for sigma receptors are psychoses (schizophrenia), hallucinations in combination with psychotic disorders and chronic psychological depressions, psychoneuroses, brain function disorders (cerebral ischemia, cognitive dysfunction), disorders of intestinal function (absorption, secretion, motility) and of other smooth muscular organs, such as vas deferens and bladder (urinary incontinence), and other disorders such as are connected with affinities for sigma receptors and such as are described, for example, in the literature surveys of B. L. Largent et al. (Eur. J. Pharmacol., 155, 345–7, 1988), S. I. Deutsch et al. (Clinical Neuropharmacology, 11(2), 105–119, 1988), T. P. Su (Eur. J. Biochem., 200, 633–642, 1991) and J. M. Walker et al. (Pharmacol. Rev. 42, 355–402, 1990).

In the use according to the invention of the compounds of the formula I for the production of the abovementioned medicaments, the pharmacologically active compounds of the formula I and/or their salts (=active compounds) are processed with suitable pharmaceutical auxiliaries or excipients to give tablets, coated tablets, capsules, suppositories, patches (e.g. as TTS), emulsions, suspensions or solutions, the active compound content advantageously being between 0.1 and 95% and it being possible to achieve a pharmaceutical administration form (e.g. a delayed release form or an enteric form) exactly matched to the active compound and/or to the desired onset of action by the appropriate choice of the auxiliaries and excipients.

The person skilled in the art is familiar on the basis of his expert knowledge with the auxiliaries or excipients which are suitable for the desired pharmaceutical formulations. Apart from solvents, gel-forming agents, suppository bases, tablet auxiliaries and other excipients, it is possible to use, for example, antioxidants, dispersants, emulsifiers, antifoams, flavor corrigents, preservatives, solubilizers, colorants or in particular permeation promoters and complexing agents (e.g. cyclodextrins).

The active compounds can be administered orally, rectally, parenterally or percutaneously.

In general, it has proven advantageous in human medicine to administer the active compound(s) in the case of oral administration in a daily dose from approximately 0.01 to approximately 20, preferably 0.05 to 5, in particular 0.2 to 2.0, mg/kg of body weight, if appropriate in the form of several, preferably 1 to 4, individual doses to achieve the desired result. In a parenteral treatment, it is possible to use similar or (in particular in the intravenous administration of the active compounds) generally lower doses. Any person skilled in the art can easily determine the optimum dose necessary in each case and manner of administration of the active compounds on the basis of his expert knowledge.

If the compounds of the formula I and/or salts are employed for the treatment of sigma receptor-modulated illnesses, the pharmaceutical preparations can also contain one or more pharmacologically active constituents of other pharmaceutical groups.

The invention furthermore includes the use of the compounds according to the invention for the treatment of sigma receptor-modulated illnesses.

One embodiment of the invention is the use of compounds of the formula I in which
R1 is phenyl,
R2 is phenyl,
R3 is hydrogen or 1–4C-alkyl,
R4 is hydrogen or 1–4C-alkyl,
R5 is hydrogen or 1–4C-alkyl,
m is the number 2
and
n is the number 0.

A further embodiment of the invention is the use of compounds of the formula I in which
R1 is hydrogen,
R2 is hydrogen,
R3 is phenyl,
R4 is cyclopentyl, cyclohexyl, phenyl, 2-norbornen-5-yl or tricyclo[2.2.1.0$^{2,6}$]hept-2-yl,
R5 is hydroxyl
m is the number 1 or 2
and
n is the number 2 or 3.

A further embodiment of the invention is the use of compounds of the formula I in which R1 is phenyl, R2 is phenyl, R3 is hydrogen, R4 is methyl, R5 is methyl, m is the number 2 and n is the number 0, and their salts for the production of medicaments for the treatment of sigma receptor-modulated illnesses.

A further embodiment of the invention is the use of compounds of the formula I in which R1 is phenyl, R2 is phenyl, R3 is methyl, R4 is methyl, R5 is methyl, m is the number 2 and n is the number 0, and their salts for the production of medicaments for the treatment of sigma receptor-modulated illnesses.

A further embodiment of the invention is the use of compounds of the formula I in which R1 is hydrogen, R2 is hydrogen, R3 is phenyl, R4 is 2-norbornen-5-yl, R5 is hydroxyl, m is the number 2 and n is the number 2, and their salts for the production of medicaments for the treatment of sigma receptor-modulated illnesses.

A further embodiment of the invention is the use of compounds of the formula I in which R1 is hydrogen, R2 is hydrogen, R3 is phenyl, R4 is cyclopentyl, R5 is hydroxyl, m is the number 2 and n is the number 2, and their salts for the production of medicaments for the treatment of sigma receptor-modulated illnesses.

A further embodiment of the invention is the use of compounds of the formula I in which R1 is hydrogen, R2 is hydrogen, R3 is phenyl, R4 is phenyl, R5 is hydroxyl, m is the number 2 and n is the number 2, and their salts for the production of medicaments for the treatment of sigma receptor-modulated illnesses.

A further embodiment of the invention is the use of compounds of the formula I in which R1 is hydrogen, R2 is hydrogen, R3 is phenyl, R4 is cyclohexyl, R5 is hydroxyl, m is the number 1 and n is the number 2, and their salts for the production of medicaments for the treatment of sigma receptor-modulated illnesses.

A further embodiment of the invention is the use of compounds of the formula I in which R1 is hydrogen, R2 is hydrogen, R3 is phenyl, R4 is cyclohexyl, R5 is hydroxyl, m is the number 2 and n is the number 2, and their salts for the production of medicaments for the treatment of sigma receptor-modulated illnesses.

A further embodiment of the invention is the use of compounds of the formula I in which R1 is hydrogen, R2 is hydrogen, R3 is phenyl, R4 is tricyclo[2.2.1.0$^{2,6}$]hept-2-yl, R5 is hydroxyl, m is the number 2 and n is the number 2, and their salts for the production of medicaments for the treatment of sigma receptor-modulated illnesses.

A further embodiment of the invention is the use of compounds of the formula I in which R1 is hydrogen, R2 is hydrogen, R3 is phenyl, R4 is phenyl, R5 is hydroxyl, m is the number 2 and n is the number 3, and their salts for the production of medicaments for the treatment of sigma receptor-modulated illnesses.

The compounds of the formula I are known, for example from the patent specifications mentioned in the prior art.

Pharmacology

The affinity and selectivity of the compounds described above in greater detail for sigma receptors in comparison with NMDA receptors were determined following published methods (Kornhuber et al.: Eur. J. Pharmacol. 162, 483–490, 1989 and Neurosci. Lett. 163, 129–131, 1993). The table shows the exemplary comparison of the compound budipine with aminoadamantane derivatives, which are also employed for the therapy of Parkinsonism. A higher affinity and selectivity (lower $K_i$ value) of budipine for sigma receptors has now surprisingly been found.

| $K_i$ values ($\mu$M) | Sigma receptors (pentazocine binding) | NMDA receptors (MK 801 binding) |
| --- | --- | --- |
| Budipine | 2.0 | 11.7 |
| Amantadine | 20.3 | 10.5 |
| Memantine | 20.0 | 0.5 |

We claim:

1. In a method for treating a sigma receptor-modulated illness which comprising administering an effective amount of an active compound to a subject in need of such treatment, the improvement wherein the active compound is a compound of formula I

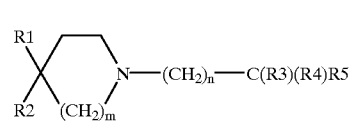

(I)

in which
R1 is phenyl,
R2 is phenyl
R3 is hydrogen or 1-4C-alkyl,
R4 is hydrogen or 1-4C-alkyl,
R5 is hydrogen or 1-4C-alkyl,
m is the number 2
and n is the number 0,
or a pharmacologically-acceptable salt thereof.

2. A method as claimed in claim 1 wherein the active compound is budipine and wherein the illness is a psychosis.

3. A method as claimed in claim 1 wherein the compound is budipine and the illness is a brain function disorder.

4. A method of claim 3 wherein the brain function disorder is cerebral ischemia or cognitive dysfunction.

5. A method as claimed in claim 1 wherein the compound is budipine and the illness is an intestinal function disorder.

6. A method of claim 5 wherein the intestinal function disorder is absorption, secretion or motility.

7. A method as claimed in claim 1 wherein the compound is budipine and the illness is an urogenital tract disorder.

8. A method of claim 7 wherein the urogenital tract disorder is urinary incontinence.

* * * * *